US007294489B2

(12) United States Patent
Brentano et al.

(10) Patent No.: US 7,294,489 B2
(45) Date of Patent: Nov. 13, 2007

(54) **NUCLEIC ACID AMPLIFICATION AND DETECTION OF *MYCOBACTERIUM* SPECIES**

(75) Inventors: Steven T. Brentano, Santee, CA (US); Markus T. Jucker, Poway, CA (US); Francisco D. Delgado, San Diego, CA (US); Philippe Cleuziat, Lyons (FR); Marc Rodrigue, Dardilly (FR)

(73) Assignees: Gen-Probe Incorporated, San Diego, CA (US); BioMerieux S.A., Marcy-l'Etoile (FR)

( * ) Notice: Subject to any disclaimer, the term of this patent is extended or adjusted under 35 U.S.C. 154(b) by 436 days.

(21) Appl. No.: 10/665,708

(22) Filed: Sep. 18, 2003

(65) Prior Publication Data

US 2005/0100915 A1 May 12, 2005

Related U.S. Application Data

(62) Division of application No. 09/738,274, filed on Dec. 15, 2000, now Pat. No. 6,664,081.

(60) Provisional application No. 60/172,190, filed on Dec. 17, 1999.

(51) Int. Cl.
*C12P 19/34* (2006.01)
*C07H 21/04* (2006.01)

(52) U.S. Cl. ............... 435/91.2; 435/6; 536/24.32; 536/24.3

(58) Field of Classification Search ................ None
See application file for complete search history.

(56) References Cited

U.S. PATENT DOCUMENTS

| | | | |
|---|---|---|---|
| 5,422,242 A | 6/1995 | Young | |
| 5,521,300 A | 5/1996 | Shah et al. | |
| 5,554,516 A | 9/1996 | Kacian et al. | |
| 5,561,044 A | 10/1996 | Walker et al. | |
| 5,574,145 A | 11/1996 | Barry et al. | |
| 5,677,128 A * | 10/1997 | Hogan et al. ........... | 435/6 |
| 5,712,095 A | 1/1998 | Britschgi et al. | |
| 5,726,021 A | 3/1998 | Britschgi et al. | |
| 5,766,849 A | 6/1998 | McDonough et al. | |
| 5,851,763 A | 12/1998 | Heym et al. | |
| 5,906,917 A | 5/1999 | Hammond | |
| 5,908,744 A * | 6/1999 | McAllister et al. ...... | 435/6 |
| 5,925,518 A | 7/1999 | Earle et al. | |
| 5,985,569 A | 11/1999 | Foxall et al. | |
| 6,001,611 A | 12/1999 | Will | |
| 6,110,678 A | 8/2000 | Weisburg et al. | |
| 6,136,529 A | 10/2000 | Hammond | |
| 6,207,883 B1 | 3/2001 | Baudot et al. | |
| 6,280,952 B1 | 8/2001 | Weisburg et al. | |
| 6,475,793 B1 | 11/2002 | Rosenthal et al. | |

2002/0137035 A1 9/2002 Stender et al.

FOREIGN PATENT DOCUMENTS

WO WO99/35284 A1 7/1999
WO WO01/66797 A2 9/2001

OTHER PUBLICATIONS

Buck et al. (BioTechniques, 27:528-536, Sep. 1999).*
Kazda et al. (International Journal of Systemic Bacteriology, Jul. 1990, p. 217-223).*
GenBank X53896, GI: 44201, published Sep. 4, 1991.*
Boddinghaus et al., "Detection and Identification of Mycobacteria by Amplification of rRNA", J. Clin. Microbiol., Aug. 1990, 28(8):1751-9, American Society for Microbiology, U.S.
Fauville-Dufaux et al., "Rapid Identification of *Mycobacterium xenopi* from bacterial colonies of "Bactec" culture by the polymerase chain reaction and a luminescent sandwich hybridization assay", Res. Microbiol., May 1995, 146(4):349-56, Institute Pasteur/Elsevier, Paris, France.
Gingeras et al., "Simultaneous Genotyping and Species Identification Using Hybridization Pattern Recognition Analysis of Generic *Mycobacterium* DNA Arrays", Genome Res., May 1998, 8(5):435-48, Cold Spring Harbor Press, U.S.
Holberg-Petersen et al., "Identification of clinical isolates of *Mycobacterium* spp. by sequence analysis of the 16S ribosomal RNA gene. Experience from a clinical laboratory" Acta Pathologica Microbiologica et Immunologica, Feb. 1999, 107(2):231-9, APMIS, Scandinavia.
Kirschner et al., "Diagnosis of Mycobacterial Infrections by Nucleic Acid Amplification: 18-Month Prospective Study", J. Clin. Microbiol., Feb. 1996, 34(2):304-12, American Society for Microbiology, U.S.
Kirschner et al, "Genotypic Identification and Detection of Mycobacteria—Facing Novel and Uncultured Pathogens", Diagnostic Molecular Biology—Principles and Applications, Pershing et al., Eds., 1993, Pt. II, Sect. 1.1:173-190, American Society For Microbiology, US.
Kirschner et al., "Species identification of mycobacteria using rDNA sequencing", Methods Mol. Biol. 1998, 101:349-61, Elsevier, G.B.
Klemen et al., "Multiplex polymerase chain reaction for rapid detection of atypical mycobacteria and *Mycobacterium tuberculosis* complex" Diagn. Mol. Pathol. Dec. 1998, 7(6):310-6, Lippincott Williams & Wilkins, U.S.
Kox et al., "Microwell Hybridization Assay for Detection of PCR Products from *Mycobacterium tuberculosis* Complex and the Recombinant *Mycobacterium smegmatis* Strain 1008 Used as an Inernal Control", J. Clin. Microbiol., Sep. 1996, 34(9):2117-20, American Society for Microbiology, U.S.
Rogall et al., "Towards a phylogeny and definition of species at the molecular level within the genus *Mycobacterium*", Int. J. of Syst. Bacteriol., Oct. 1990, 40(4):323-30, American Society for Microbiology, U.S.

(Continued)

*Primary Examiner*—Juliet C. Switzer
(74) *Attorney, Agent, or Firm*—Christine A. Gritzmacher

(57) ABSTRACT

Oligonucleotides used to prime in vitro nucleic acid amplification of 16S rRNA sequences or DNA encoding 16S rRNA sequences for many species within the genus *Mycobacterium* are disclosed. Kits including such oligonucleotides are disclosed. Methods of detecting *Mycobacterium* species using the oligonucleotides in in vitro nucleic acid amplification are disclosed.

20 Claims, No Drawings

OTHER PUBLICATIONS

Stackebrant et al., "Taxonomic Note: A Place for DNA-DNA Reassociation and 16S rRna Sequence Analysis in the Present Species Definition in Bacteriology", Int. J. of Syst. Bacteriol., Oct. 1994, 44(4):846-9, International Union of Microbiological Societies, U.S.

Suzuki et al., "Complete Nucleotide Sequence of the 16S rRNA gene of *Mycrobacterium bovis* BCG", J. Bacteriol., 1988, 170:2886-9, American Society for Microbiology, U.S.

Troesch et al., "*Mycobacterium* Species Identification and Rifampin Resistance Testing with High-Density DNA Probe Arrays", J. Clin. Microbiol., Jan. 1999, 37(1):49-55, American Society for Microbiology, U.S.

Kirschner et al., "Genotypic Identification of Mycobacteria by Nucleic Acid Sequence Determination: Report of a 2-Year Experience in a Clinical Laboratory," J. Clin. Microbiol., 1993, 31(11):2882-2889, ASM, Washington, D.C., USA.

* cited by examiner

SEQUENCE LISTING

<160> NUMBER OF SEQ ID NOS: 42

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 1
gcccattgtg caatattccc cact                                          24

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 2
tgtgcaatat tccccactgc tgcct                                         25

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 3
cccattgtgc aatattcccc actgct                                        26

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 4
ccattgtgca atattcccca ctgc                                          24

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 5
ttgtgcaata ttccccactg c                                             21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 6

```
tgcatcaggc ttgcgccca                                                      19
```

<210> SEQ ID NO 7
<211> LENGTH: 57
<212> TYPE: DNA
<213> ORGANISM: Artificial Sequence
<220> FEATURE:
<223> OTHER INFORMATION: Description of Artificial Sequence: primer
      oligonucleotide
<220> FEATURE:
<221> NAME/KEY: promoter
<222> LOCATION: (1)..(33)

<400> SEQUENCE: 7

```
gaaattaata cgactcacta tagggagacc acagcccatt gtgcaatatt ccccact         57
```

<210> SEQ ID NO 8
<211> LENGTH: 58
<212> TYPE: DNA
<213> ORGANISM: Artificial Sequence
<220> FEATURE:
<223> OTHER INFORMATION: Description of Artificial Sequence: primer
      oligonucleotide
<220> FEATURE:
<221> NAME/KEY: promoter
<222> LOCATION: (1)..(33)

<400> SEQUENCE: 8

```
gaaattaata cgactcacta tagggagacc acatgtgcaa tattccccac tgctgcct       58
```

<210> SEQ ID NO 9
<211> LENGTH: 59
<212> TYPE: DNA
<213> ORGANISM: Artificial Sequence
<220> FEATURE:
<223> OTHER INFORMATION: Description of Artificial Sequence: primer
      oligonucleotide
<220> FEATURE:
<221> NAME/KEY: promoter
<222> LOCATION: (1)..(33)

<400> SEQUENCE: 9

```
gaaattaata cgactcacta tagggagacc acacccattg tgcaatattc cccactgct     59
```

<210> SEQ ID NO 10
<211> LENGTH: 57
<212> TYPE: DNA
<213> ORGANISM: Artificial Sequence
<220> FEATURE:
<223> OTHER INFORMATION: Description of Artificial Sequence: primer
      oligonucleotide
<220> FEATURE:
<221> NAME/KEY: promoter
<222> LOCATION: (1)..(33)

<400> SEQUENCE: 10

```
gaaattaata cgactcacta tagggagacc acaccattgt gcaatattcc ccactgc         57
```

<210> SEQ ID NO 11
<211> LENGTH: 54
<212> TYPE: DNA
<213> ORGANISM: Artificial Sequence
<220> FEATURE:
<223> OTHER INFORMATION: Description of Artificial Sequence: primer
      oligonucleotide
<220> FEATURE:
<221> NAME/KEY: promoter
<222> LOCATION: (1)..(33)

-continued

<400> SEQUENCE: 11
gaaattaata cgactcacta tagggagacc acattgtgca atattcccca ctgc           54

<210> SEQ ID NO 12
<211> LENGTH: 52
<212> TYPE: DNA
<213> ORGANISM: Artificial Sequence
<220> FEATURE:
<223> OTHER INFORMATION: Description of Artificial Sequence: primer
      oligonucleotide
<220> FEATURE:
<221> NAME/KEY: promoter
<222> LOCATION: (1)..(33)

<400> SEQUENCE: 12
gaaattaata cgactcacta tagggagacc acatgcatca ggcttgcgcc ca             52

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 13
gtgcttaaca catgcaagtc gaacgga                                         27

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 14
gcaagtcgaa cggaaaggtc tcttcggaga ta                                   32

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 15
cgaacggaaa ggtctcttcg gagatact                                        28

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 16
gaacggaaag gtctcttcgg agatactc                                        28

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: primer -continued oligonucleotide

<400> SEQUENCE: 17
gaacggaaag gtctcttcgg agatacac                                                    28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: primer
    oligonucleotide

<400> SEQUENCE: 18
gaacggaaag gtctcttcgg agatgctc                                                    28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: primer
    oligonucleotide

<400> SEQUENCE: 19
gaacggaaag gtctcttcgg agatgcac                                                    28

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: primer
    oligonucleotide

<400> SEQUENCE: 20
gaacggaaag gccccttuuu ugggggtgctc                                          30

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: primer
    oligonucleotide

<400> SEQUENCE: 21
gcaagtcgaa cggaaaggcc tttcg                                                      25

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: primer
    oligonucleotide

<400> SEQUENCE: 22
caagtcgaac ggaaaggcct ttcg                                                          24

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: primer
    oligonucleotide

```
<400> SEQUENCE: 23
gtcgaacgga aaggcctttc gg                                        22

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 24
gaacggaaag gcctttcgg                                            19

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 25
gaaaggcctt tcgggggtgc tc                                        22

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 26
gaaaggcctt tcgggggtgc tcgag                                     25

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 27
caagtcgaac ggaaaggccc ctt                                       23

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 28
gtcgaacgga aaggcccctt ttttgg                                    26

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: primer
      oligonucleotide
```

-continued

<400> SEQUENCE: 29
gaacggaaag gcccctttt tgg                                        23

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 30
gaacggaaag gcccctttt tg                                         22

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 31
cggaaaggcc ccttttttg                                            19

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 32
cggaaaggcc ccttttttgg                                           20

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 33
cggaaaggcc ccttttttgg ggt                                       23

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: primer
      oligonucleotide

<400> SEQUENCE: 34
ggaaaggccc cttttttg                                             18

<210> SEQ ID NO 35
<211> LENGTH: 48
<212> TYPE: DNA
<213> ORGANISM: Artificial Sequence
<220> FEATURE:
<223> OTHER INFORMATION: Description of Artificial Sequence: Capture
      oligomer
<220> FEATURE:
<221> NAME/KEY: modified_base

```
<222> LOCATION: (1)
<223> OTHER INFORMATION: cm
<220> FEATURE:
<221> NAME/KEY: modified_base
<222> LOCATION: (2)
<223> OTHER INFORMATION: 2'-O-methoxy-thymidine
<220> FEATURE:
<221> NAME/KEY: modified_base
<222> LOCATION: (3)
<223> OTHER INFORMATION: 2'-O-methoxy-adenosine
<220> FEATURE:
<221> NAME/KEY: modified_base
<222> LOCATION: (4)
<223> OTHER INFORMATION: gm
<220> FEATURE:
<221> NAME/KEY: modified_base
<222> LOCATION: (5)
<223> OTHER INFORMATION: 2'-O-methoxy-thymidine
<220> FEATURE:
<221> NAME/KEY: modified_base
<222> LOCATION: (6)
<223> OTHER INFORMATION: cm
<220> FEATURE:
<221> NAME/KEY: modified_base
<222> LOCATION: (7)
<223> OTHER INFORMATION: 2'-O-methoxy-thymidine
<220> FEATURE:
<221> NAME/KEY: modified_base
<222> LOCATION: (8)
<223> OTHER INFORMATION: gm
<220> FEATURE:
<221> NAME/KEY: modified_base
<222> LOCATION: (9)..(11)
<223> OTHER INFORMATION: cm
<220> FEATURE:
<221> NAME/KEY: modified_base
<222> LOCATION: (12)
<223> OTHER INFORMATION: gm
<220> FEATURE:
<221> NAME/KEY: modified_base
<222> LOCATION: (13)
<223> OTHER INFORMATION: 2'-O-methoxy-thymidine
<220> FEATURE:
<221> NAME/KEY: modified_base
<222> LOCATION: (14)
<223> OTHER INFORMATION: 2'-O-methoxy-adenosine
<220> FEATURE:
<221> NAME/KEY: modified_base
<222> LOCATION: (15)
<223> OTHER INFORMATION: 2'-O-methoxy-thymidine

<400> SEQUENCE: 35
ctagtctgcc cgtattttaa aaaaaaaaaa aaaaaaaaa aaaaaaaa         48

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: promoter

<400> SEQUENCE: 36
gaaattaata cgactcacta tagggagacc aca                         33

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:  primer
      oligonucleotide

<400> SEQUENCE: 37
acggaaaggc cccttttttg                                        20
```

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: primer oligonucleotide
<220> FEATURE:
<221> NAME/KEY: modified_base
<222> LOCATION: (25)
<223> OTHER INFORMATION: K-base

<400> SEQUENCE: 38
gaacggaaag gtctcttcgg agatnctc                          28

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: probe

<400> SEQUENCE: 39
gtcttgtggt ggaaagcgct ttag                              24

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: probe

<400> SEQUENCE: 40
ggacctcaag acgcatgtc                                    19

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: probe

<400> SEQUENCE: 41
taggaccatt ctgcgcatgt g                                 21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: probe

<400> SEQUENCE: 42
taggaccact tggcgcatgc c                                 21

NUCLEIC ACID AMPLIFICATION AND DETECTION OF MYCOBACTERIUM SPECIES

RELATED APPLICATIONS

This application is a divisional of U.S. application Ser. No. 09/738,274, filed Dec. 15, 2000 now U.S. Pat. No 6,664,081, and claims the benefit under 35 U.S.C. §119(e) of U.S. Provisional Application No. 60/172,190, filed Dec. 17, 1999, the contents of both of which are hereby incorporated by reference.

FIELD OF THE INVENTION

This invention relates to in vitro diagnostic detection of pathogenic bacteria, and specifically relates to compositions and assays for detecting many species of Mycobacterium by using in vitro nucleic acid amplification and detection of amplified products.

BACKGROUND OF THE INVENTION

Detection of Mycobacterium species in clinical species is important as a clinical diagnostic tool. Historically, M. tuberculosis was thought to be the only clinically significant pathogen in this genus. A rise in the incidence of drug-resistant strains of M. tuberculosis has further emphasized the need to detect this species. Other Mycobacterium species, however, are also clinically important. These are sometimes referred to as "MOTT" for Mycobacterium other than tuberculosis, commonly including M. avium/intracellulare complex organisms (M. avium, M. intracellulare, M. paratuberculosis, commonly referred to as MAIC), M. gordonae, M. fortuitum, M. chelonae, M. mucogenicum and mixtures of Mycobacterium species in a clinical specimen. For example, fast-growing opportunistic infections by M. avium complex (MAC) bacteria have been shown to occur frequently in AIDS and other immunocompromised individuals. In such infected individuals, at least $10^6$ MAC cells/ml of sputum sediment have been found. Therefore, detection assays that can detect, and optimally distinguish between, many species of Mycobacterium are clinically important.

Many clinical methods for detecting and identifying Mycobacterium species in samples require analysis of the bacteria's physical characteristics (e.g., acid-fast staining and microscopic detection of bacilli), physiological characteristics (e.g., growth on defined media) or biochemical characteristics (e.g., membrane lipid composition). These methods require relatively high concentrations of bacteria in the sample to be detected, may be subjective depending on the clinical technician's experience and expertise, and are time-consuming. Because Mycobacterium species are often difficult to grow in vitro and may take several weeks to reach a useful density in culture, these methods can also result in delayed patient treatment and costs associated with isolating an infected individual until the diagnosis is completed.

More recently, assays that detect the presence of nucleic acid derived from bacteria in the sample have been preferred because of the sensitivity and relative speed of the assays. In particular, assays that use in vitro nucleic acid amplification of nucleic acids present in a clinical sample can provide increased sensitivity and specificity of detection. Such assays, however, can be limited to detecting one or a few Mycobacterium species depending on the sequences amplified and/or detected.

Assays and reagents for detecting Mycobacterium nucleic acid sequences have been previously disclosed, for example, in U.S. Pat. Nos. 5,554,516, 5,766,849, 5,795,752, 5,906, 917, 5,908,744; European Patent Nos. EP 0528306 and EP 0818465; and published PCT Patent Applications WO 9636733 and WO 9723618.

The present invention provides compositions and relatively simple diagnostic methods that detect a wide spectrum of Mycobacterium species that may be present in a clinical sample.

SUMMARY OF THE INVENTION

According to one aspect of the invention, there is provided a method of detecting Mycobacterium species present in a biological sample. The method includes the steps of providing a biological sample containing nucleic acid from at least one Mycobacterium species comprising a Mycobacterium 16S ribosomal RNA (rRNA) or a DNA encoding the Mycobacterium 16S ribosomal rRNA; amplifying the Mycobacterium 16S rRNA or DNA in an in vitro nucleic acid amplification mixture comprising at least one polymerase activity, and at least two primers having sequences selected from the group consisting of SEQ ID NO:1 to SEQ ID NO: 34, SEQ ID NO:37 and SEQ ID NO:38 to produce amplified Mycobacterium nucleic acid; and detecting the amplified Mycobacterium nucleic acid by detecting a label associated with the amplified Mycobacterium nucleic acid. In one embodiment, the method also includes the steps of adding to the biological sample at least one capture oligonucleotide that specifically hybridizes to the Mycobacterium 16S rRNA and an immobilized nucleic acid that hybridizes to the capture oligonucleotide under hybridizing conditions to produce a hybridization complex; and separating the hybridization complex from other components of the biological sample before the amplifying step. In preferred embodiments, the amplifying step amplifies 16S rRNA or DNA of M. tuberculosis or a Mycobacterium other than tuberculosis (MOTT) species. In other preferred embodiments, the amplifying step amplifies 16S rRNA or DNA of M. abscessus, M. africanum, M. asiaticum, M. avium, M. bovis, M. celatum, M. chelonae, M. flavescens, M. fortuitum, M. gastri, M. gordonae, M. haemophilum, M. intracellulare, M. interjectum, M. intermedium, M. kansasii, M. malmoense, M. marinum, M. non-chromogenicum, M. paratuberculosis, M. phlei, M. scrofulaceum, M. shimodei, M. simiae, M. smegmatis, M. szulgai, M. terrae, M. triviale, M. tuberculosis, M. ulcerans or M. xenopi. In another embodiment, the detecting step uses at least one probe that hybridizes specifically to the amplified Mycobacterium nucleic acid. The detecting step may use at least one labeled probe that hybridizes specifically to the amplified Mycobacterium nucleic acid or may use a plurality of probes that hybridize specifically to the amplified Mycobacterium nucleic acid. In preferred embodiments, the amplifying step uses a combination of at least a first primer and a second primer, wherein the first primer is selected from the group consisting of SEQ ID NO:1 to SEQ ID NO:12, and the second primer is selected from the group consisting of SEQ ID NO:13 to SEQ ID NO:34, SEQ ID NO:37 and SEQ ID NO:38. Additional embodiments in the amplifying step use a combination of at least a first primer and a second primer, wherein the first primer is selected from the group consisting of SEQ ID NO:7 to SEQ ID NO:12, and the second primer is selected from the group consisting of SEQ ID NO:13 to SEQ ID NO:34, SEQ ID NO:37 and SEQ ID NO:38. Preferred combinations of first and second primer used in the amplifying step are: the first primer has the sequence of SEQ ID NO:7, and the second primer has the sequence of SEQ ID NO:13; the first primer has the sequence of SEQ ID NO:7, and the second primer has the sequence of SEQ ID NO:14; the first primer has the sequence of SEQ ID NO:7, and the second primer has the sequence of SEQ ID NO:15; the first primer has the sequence of SEQ ID NO:7, and the second primer has the sequence of SEQ ID NO:16; the first primer has the sequence of SEQ ID NO:8, and the second primer has the sequence of SEQ ID NO:13; the first primer has the sequence of SEQ ID NO:8, and the second primer has the sequence of SEQ ID NO:14; the first primer has the sequence of SEQ ID NO:8, and the second primer has the sequence of SEQ ID NO:15; the first primer has the sequence of SEQ ID NO:9, and the second primer has the sequence of SEQ ID NO:13; the first primer has the sequence of SEQ ID NO:9, and the second primer has the sequence of SEQ ID NO:14; the first primer has the sequence of SEQ ID NO:9, and the second primer has the sequence of SEQ ID NO:15; the first primer has the sequence of SEQ ID NO:10, and the second primer has the sequence of SEQ ID NO:16; the first primer has the sequence of SEQ ID NO:11, and the second primer has the sequence of SEQ ID NO:13; the first primer has the sequence of SEQ ID NO:11, and the second primer has the sequence of SEQ ID NO:16; the first primer has the sequence of SEQ ID NO:11, and the second primer has the sequence of SEQ ID NO:17; the first primer has the sequence of SEQ ID NO:11, and the second primer has the sequence of SEQ ID NO:18; the first primer has the sequence of SEQ ID NO:11, and the second primer has the sequence of SEQ ID NO:19; the first primer has the sequence of SEQ ID NO:11, and the second primer has the sequence of SEQ ID NO:20; or the first primer has the sequence of SEQ ID NO:12, and the second primer has the sequence of SEQ ID NO:15. In one embodiment, the amplifying step uses a combination of at least a first primer and a second primer, wherein the first primer has the sequence of SEQ ID NO:11, and the second primer has the sequence of SEQ ID NO:16, SEQ ID NO:30 or SEQ ID NO:37. In another embodiment, the amplifying step uses a combination of a first primer having the sequence of SEQ ID NO:11, and two second primers, one second primer having the sequences SEQ ID NO:16 and the other second primer having the sequence of SEQ ID NO:37.

Another aspect of the invention is a composition for amplifying in an in vitro amplification reaction a *Mycobacterium* 16S rRNA sequence or a DNA encoding the *Mycobacterium* 16S rRNA, comprising one or more oligonucleotides having a base sequence selected from the group consisting of SEQ ID NO:1 to SEQ ID NO: 34, SEQ ID NO:37 and SEQ ID NO:38. In preferred embodiments, the composition includes at least one first oligonucleotide containing the sequence of any one of SEQ ID NO:1 to SEQ ID NO:12, and at least one second oligonucleotide containing the sequence of any one of SEQ ID NO:13 to SEQ ID NO:34, SEQ ID NO:37 or SEQ ID NO:38. In another embodiment, the composition includes at least one first oligonucleotide containing the sequence of any one of SEQ ID NO:7 to SEQ ID NO:12, and at least one second oligonucleotide containing the sequence of any one of SEQ ID NO:13 to SEQ ID NO:34, SEQ ID NO:37 or SEQ ID NO:38.

Another aspect of the invention is a kit containing any of the oligonucleotides having a base sequence selected from the group consisting of SEQ ID NO:1 to SEQ ID NO: 34, SEQ ID NO:37 and SEQ ID NO:38. In preferred embodiments, the kit includes at least one first oligonucleotide containing the sequence of any one of SEQ ID NO:1 to SEQ ID NO:12, and at least one second oligonucleotide containing the sequence of any one of SEQ ID NO:13 to SEQ ID NO:34, SEQ ID NO:37 or SEQ ID NO:38. In another embodiment, the kit includes at least one first oligonucleotide containing the sequence of any one of SEQ ID NO:7 to SEQ ID NO:12, and at least one second oligonucleotide containing the sequence of any one of SEQ ID NO:13 to SEQ ID NO:34, SEQ ID NO:37 or SEQ ID NO:38.

DETAILED DESCRIPTION

The present invention includes methods of detecting *Mycobacterium* nucleic acids, specifically 16S rRNA sequences, present in biological samples derived from humans, preferably in processed sputum samples. The present invention also includes compositions which include nucleic acid oligomers ("capture oligonucleotides") used to specifically capture *Mycobacterium* 16S rRNA sequences present in a biological sample, amplification nucleic acid oligomers ("primers") used to specifically amplify selected portions of the captured 16S rRNA sequences and nucleic acid oligomers ("probes" or "labeled probes") for detecting amplified *Mycobacterium* sequences.

The nucleic acid sequences of this invention are useful for capturing, amplifying and detecting *Mycobacterium* nucleic acid present in a biological sample containing any of a variety of *Mycobacterium* species. The methods of the present invention are valuable for detecting *Mycobacterium* nucleic acid in a biological sample, and thus are important for diagnosis of infection that might result from a number of *Mycobacterium* species. These methods are especially important for screening for opportunistic infections by MOTT species, or *M. tuberculosis* infections.

To aid in understanding terms used in describing the invention, the following definitions are provided.

By "biological sample" is meant any tissue or material derived from a living or dead human which may contain *Mycobacterium* nucleic acid. Samples include, for example, sputum, respiratory tissue or exudates, peripheral blood, plasma or serum, cervical swab samples, biopsy tissue, gastrointestinal tissue, urine, feces, semen or other body fluids, tissues or materials. Samples also include bacterial cultures (liquid or on a solid media) and environmental samples. The biological sample may be treated to physically disrupt tissue or cell structure, thus releasing intracellular components into a solution which may further contain enzymes, buffers, salts, detergents and the like which are used to prepare the sample for analysis.

By "nucleic acid" is meant a multimeric compound comprising nucleosides or nucleoside analogs which have nitrogenous heterocyclic bases, or base analogs, where the nucleosides are covalently linked via a backbone structure to form a polynucleotide. Conventional ribonucleic acid (RNA) and deoxyribonucleic acid (DNA) are included in the term "nucleic acid" as are analogs thereof. A nucleic acid backbone may comprise a variety of linkages known in the art, including one or more of sugar-phosphodiester linkages, peptide-nucleic acid bonds (referred to as "peptide nucleic acids"; Hydig-Hielsen et al., PCT Int'l Pub. No. WO 95/32305), phosphorothioate linkages, methylphosphonate linkages or combinations thereof. Sugar moieties of the nucleic acid may be either ribose or deoxyribose, or similar compounds having known substitutions, e.g., 2' methoxy substitutions and/or 2' halide substitutions. Nitrogenous bases may be conventional bases (A, G, C, T, U), known analogs thereof (e.g., inosine or others; see *The Biochemistry of the Nucleic Acids* 5-36, Adams et al., ed., 11$^{th}$ ed., 1992), or known derivatives of purine or pyrimidine bases (see, Cook, PCT Int'l Pub. No. WO 93/13121) and "abasic" residues in which the backbone includes no nitrogenous base for one or more residues (Arnold et al., U.S. Pat. No. 5,585,481). A nucleic acid may comprise only conventional sugars, bases and linkages, as found in RNA and DNA, or may include both conventional components and substitutions (e.g., conventional bases linked via a methoxy backbone, or a nucleic acid including conventional bases and one or more base analogs).

By "oligonucleotide" or "oligomer" is meant a nucleic acid having generally less than 1,000 residues, including polymers in a size range having a lower limit of about 2 to 5 nucleotide residues and an upper limit of about 500 to 900 nucleotide residues. Preferred oligomers are in a size range having a lower limit of about 5 to about 15 residues and an upper limit of about 50 to 600 residues; more preferably, in a size range having a lower limit of about 10 residues and an upper limit of about 100 residues. Oligomers may be purified from naturally occurring sources, but preferably are synthesized using well known methods.

By "amplification oligonucleotide" or "amplification oligomer" is meant an oligonucleotide that hybridizes to a target nucleic acid, or its complement, and participates in an in vitro nucleic acid amplification reaction (e.g., primers and promoter primers). Preferably, an amplification oligonucleotide contains at least about 10 contiguous bases, and more preferably at least about 12 contiguous bases, which are complementary to a region of the target nucleic acid sequence (or a complementary strand thereof). The contiguous bases are preferably at least 80%, more preferably at least 90% complementary to the sequence to which the amplification oligonucleotide binds. An amplification oligonucleotide is preferably about 10 to about 60 bases long and may include modified nucleotides or base analogs.

Amplification oligonucleotides and oligomers may be referred to as "primers" or "promoter-primers." A "primer" refers to an oligonucleotide which is capable of hybridizing to a template nucleic acid and which has a 3' end that is extended in a polymerization reaction, usually mediated by an enzyme. The 5' region of the primer may be non-complementary to the target nucleic acid and include additional bases, such as a promoter sequence. Such a primer is referred to as a "promoter-primer." Those skilled in the art will appreciate that any oligomer that can function as a primer can be modified to include a 5' promoter sequence, and thus could function as a promoter primer. Similarly, any promoter primer can serve as a primer, independent of its promoter sequence function.

By "amplification" is meant any known in vitro procedure for obtaining multiple copies of a target nucleic acid sequence or its complement or fragments thereof. In vitro amplification refers to production of an amplified nucleic acid that may contain less than the complete target region sequence or its complement. Known amplification methods include, for example, transcription-mediated amplification, replicase-mediated amplification, polymerase chain reaction (PCR) amplification, ligase chain reaction (LCR) amplification and strand-displacement amplification (SDA). Replicase-mediated amplification uses self-replicating RNA molecules, and a replicase such as QB-replicase (Kramer et al., U.S. Pat. No. 4,786,600; PCT Int'l Pub. No. WO 90/14439). PCR amplification is well known and uses DNA polymerase, primers and thermal cycling to synthesize multiple copies of the two complementary strands of DNA or cDNA (Mullis et al., U.S. Pat. Nos. 4,683,195, 4,683,202, and 4,800,159; *Methods in Enzymology,* 1987, Vol. 155: 335-350). LCR amplification uses at least four separate oligonucleotides to amplify a target and its complementary strand by using multiple cycles of hybridization, ligation, and denaturation (EP Pat. App. Pub. No. 0 320 308). SDA is a method in which a primer contains a recognition site for a restriction endonuclease such that the endonuclease will nick one strand of a hemimodified DNA duplex that includes the target sequence, followed by amplification in a series of primer extension and strand displacement steps (Walker et al, 1992, *Proc. Natl. Acad. Sci. USA* 89:392-396; and U.S. Pat. No. 5,422,252). Transcription-mediated amplification is a preferred embodiment of the present invention. Those skilled in the art will understand that the oligonucleotide primer sequences of the present invention may be readily used in any in vitro amplification method based on primer extension by a polymerase.

By "transcription-mediated amplification" or "transcription-associated amplification" is meant any type of nucleic acid amplification that uses an RNA polymerase to produce multiple RNA transcripts from a nucleic acid template. Transcription-mediated amplification ("TMA") generally employs an RNA polymerase activity, a DNA polymerase activity, deoxyribonucleoside triphosphates, ribonucleoside triphosphates, and a promoter primer and a second non-promoter primer, and optionally may include one or more additional oligonucleotides (sometimes referred to as "helpers"). Transcription-associated amplification methods are well known in the art, as disclosed in detail elsewhere (Kacian et al., U.S. Pat. Nos. 5,399,491 and 5,554,516; Kacian et al., PCT Int'l Pub. No. WO 93/22461; Burg et al., U.S. Pat. No. 5,437,990; Gingeras et al., PCT Int'l Pub. Nos. WO 88/01302 and WO 88/10315; Malek et al., U.S. Pat. No. 5,130,238; Urdea et al., U.S. Pat. Nos. 4,868,105 and 5,124,246; McDonough et al., PCT Int'l Pub. No. WO 94/03472; and Ryder et al., PCT Int'l Pub. No. WO 95/03430). Preferred transcription-mediated amplification methods of the present invention are those disclosed by Kacian et al. (U.S. Pat. Nos. 5,399,491 and 5,554,516; PCT Application No. WO 93/22461).

By "probe" is meant a nucleic acid oligomer that hybridizes specifically to a target sequence in a nucleic acid or its complement, preferably in an amplified nucleic acid, under conditions that promote hybridization, thereby allowing detection of the target sequence or amplified nucleic acid. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). A probe's "target" generally refers to a sequence within (i.e., a subset of) an amplified nucleic acid sequence which hybridizes specifically to at least a portion of a probe oligomer using standard hydrogen bonding (i.e., base pairing). Sequences that are "sufficiently complementary" allow stable hybridization of a probe oligomer to a target sequence, even if the two sequences are not completely complementary. A probe may be labeled or unlabeled, depending on the method of detection used.

By "sufficiently complementary" is meant a contiguous nucleic acid base sequence that is capable of hybridizing to another base sequence by hydrogen bonding between a series of complementary bases. Complementary base sequences may be complementary at each position in sequence using standard base pairing (e.g., G:C, A:T or A:U pairing) or may contain one or more residues that are not complementary using standard hydrogen bonding (including abasic residues), but in which the entire complementary base sequence is capable of specifically hybridizing with another base sequence in appropriate hybridization conditions. Contiguous bases are preferably at least about 80%, more preferably at least about 90% complementary to a sequence to which an oligomer specifically hybridizes. Appropriate hybridization conditions are well known to those skilled in the art, can be predicted readily based on sequence composition and conditions, or can be determined empirically by using routine testing (see Sambrook et al., *Molecular Cloning, A Laboratory Manual*, $2^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly at §§ 9.50-9.51, 11.12-11.13, 11.45-11.47 and 11.55-11.57).

By "capture oligonucleotide" or "capture oligomer" is meant at least one nucleic acid oligomer that provides means for specifically joining a target sequence and an immobilized oligomer based on base pair hybridization (see PCT Application WO 98/50583). Generally, a capture oligomer includes two binding regions: a target-specific binding region and an immobilized probe-specific binding region Sometimes, a capture oligomer is referred to as a "capture probe."

By "immobilized probe" or "immobilized nucleic acid" is meant a nucleic acid that joins, directly or indirectly, a capture oligomer to a solid support. An immobilized probe is an oligomer joined to a solid support that facilitates separation of bound target sequence from unbound material in a sample. Any known solid support may be used, such as matrices and particles free in solution, made of any known material (e.g., nitrocellulose, nylon, glass, polyacrylate, mixed polymers, polystyrene, silane polypropylene and metal particles, preferably paramagnetic particles). Preferred supports are monodisperse paramagnetic spheres (i.e., uniform in size± about 5%), thereby providing consistent results, to which an immobilized probe is stably joined directly (e.g., via a direct covalent linkage, chelation, or ionic interaction), or indirectly (e.g., via one or more linkers), permitting hybridization to another nucleic acid in solution.

By "separating" or "purifying" is meant that one or more components of the biological sample are removed from one or more other components of the sample. Sample components include nucleic acids in a generally aqueous solution which may also include other materials (e.g., proteins, carbohydrates, lipids and/or nucleic acids). Preferably, a separating or purifying step removes at least about 70%, more preferably at least about 90% and, even more preferably, at least about 95% of the other components present in the sample.

By "label" is meant a molecular moiety or compound that can be detected or can lead to a detectable response. A label is joined, directly or indirectly, to a nucleic acid probe or to the nucleic acid to be detected (e.g., amplified product). Direct labeling can occur through bonds or interactions that link the label to the probe (e.g., covalent bonds or non-covalent interactions). Indirect labeling can occur through use of a bridging moiety or "linker", such as additional oligonucleotide(s), which is either directly or indirectly labeled. Bridging moieties can be used to amplify a detectable signal. Labels can be any known detectable moiety (e.g., a radionuclide, ligand such as biotin or avidin, enzyme or enzyme substrate, reactive group, or chromophore, such as a dye or colored particle, luminescent compond, including bioluminescent, phosphorescent or chemiluminescent compounds, and fluorescent compound). Preferably, the label on a labeled probe that is detectable in a homogeneous assay system (i.e., in a mixture, bound labeled probe exhibits a detectable change compared to unbound labeled probe). A preferred label for use in a homogenous assay is a chemiluminescent compound (see U.S. Pat. Nos. 5,656,207, 5,658, 737 and 5,639,604), more preferably an acridinium ester ("AE") compound, such as standard AE or derivatives thereof. Methods of attaching labels to nucleic acids and detecting labels are well known in the art (e.g., see Sambrook et al., *Molecular Cloning, A Laboratory Manual*, $2^{nd}$ ed. (Cold Spring Harbor Laboratory Press, Cold Spring Habor, N.Y., 1989), Chapter 10; U.S. Pat. No. 5,658,737, U.S. Pat. Nos. 5,656,207, 5,547,842, 5,283,174 and 4,581, 333; and European Pat. App. No. 0 747 706).

A "homogeneous detectable label" refers to a label whose presence can be detected in a homogeneous fashion based upon whether the label is on a probe hybridized to a target sequence. That is, a homogeneous detectable label can be detected without physically removing hybridized from unhybridized forms of the label or labeled probe. Homogeneous detectable labels and methods of detecting them have been previously described in detail (U.S. Pat. Nos. 5,283, 174, 5,656,207 and 5,658,737).

By "consisting essentially of" is meant that additional component(s), composition(s) or method step(s) that do not materially change the basic and novel characteristics of the present invention may be included in the compositions or kits or methods of the present invention. Such characteristics include the ability to detect *Mycobacterium* species rRNA sequences and/or DNA sequences encoding the rRNA in a biological sample at a copy number of about 100 or more per sample. Any component(s), composition(s), or method step(s) that have a material effect on the basic characteristics of the present invention would fall outside of this term.

Unless defined otherwise, all scientific and technical terms used herein have the same meaning as commonly understood by those skilled in the relevant art. General definitions of many of the terms used herein are provided, for example, in *Dictionary of Microbiology and Molecular Biology*, 2nd ed. (Singleton et al., 1994, John Wiley & Sons, New York, N.Y.) or *The Harper Collins Dictionary of Biology* (Hale & Marham, 1991, Harper Perennial, New York, N.Y.). Unless mentioned otherwise, the techniques employed or contemplated herein are standard methodologies well known to one of ordinary skill in the art.

The present invention includes compositions (nucleic acid capture oligomers, amplification oligomers and probes) and methods for detecting *Mycobacterium* species nucleic acid in a human biological sample. To select DNA sequences appropriate for use as capture oligomers, primers and probes, known rRNA or the corresponding genomic sequences from *M. tuberculosis*, and MOTT species, such as *M. celatum* and *M. xenopi*, including partial or complementary sequences, available from publicly accessible databases (e.g., GenBank) were aligned by matching regions of the same or similar sequences and compared using well known molecular biology techniques. Although sequence comparisons may be facilitated by using algorithms, those skilled in the art can readily perform such comparisons manually and visually. Portions of sequences containing relatively few sequence variants between the compared sequences were chosen as a basis for designing synthetic oligomers suitable for use in capture, amplification and detection of amplified sequences. Other considerations in designing oligomers included the relative GC content of the sequence (ranging from about 30-55%) and the relative absence of predicted secondary structure (e.g., hairpin structures) within a sequence, all well known in the art. Based on these analyses, the oligomers having sequences of SEQ ID NO:1 to SEQ ID NO:35 were designed and synthesized.

Target capture is preferably included in the method to increase the concentration or purity of the target nucleic acid before in vitro amplification. Preferably, target capture involves a relatively simple method of hybridizing and isolating the target nucleic acid, as described in detail in PCT Patent Application WO 98/50583. Briefly, an oligonucleotide attached to a solid support is put in contact with a mixture containing the target nucleic acid under appropriate hybridization conditions to allow the target nucleic acid to be releasably attached to the solid support. Target capture may result from direct hybridization between the target nucleic acid and the oligonucleotide attached to the solid support, or may be indirectly with one or more oligonucleotides forming a hybridization complex that links the target nucleic acid to the oligonucleotide attached to the solid support. The solid support is preferably a particle that can be readily separated from the solution, more preferably a paramagnetic particle that can be retrieved by applying a magnetic field to the vessel. Then, the target nucleic acid linked to the solid support is washed and amplified upon exposure to the appropriate primers, substrates and enzymes in an in vitro amplification reaction.

Generally, for capture oligomer sequences, the oligomer includes a sequence that specifically binds to the target sequence and a "tail" sequence used in capturing the complex to an immobilized sequence (e.g., $T_{14}$ oligomer) on the solid support. That is, the capture oligomer includes a sequence that binds specifically to *Mycobacterium* rRNA sequence which is covalently attached to a 3' tail sequence (e.g., a poly-A sequence complementary to the immobilized sequence). Any backbone to linking the base sequence of a capture oligomer may be used, but preferably the capture oligomer backbone includes O-methoxy linkages. The tail sequence (preferably 5-50 nt long) hybridizes to an immobilized complementary sequence to purify the hybridized target nucleic acid from the other sample components. A preferred capture oligomer has the sequence of SEQ ID NO:35 (CTAGTCTGCCCGTATTTT$(A)_{30}$).

Amplifying the captured target region using at least two primers can be accomplished using a variety of known nucleic acid amplification reactions, but preferably uses a transcription-associated amplification reaction. Using such an in vitro amplification method, many strands of nucleic acid are produced from a single copy of target nucleic acid, thus permitting detection of the target by specifically binding the amplified sequences to one or more detecting probes. Transcription-associated amplification has been described in detail elsewhere (Kacian et al., U.S. Pat. Nos. 5,399,491 and 5,554,516). Preferably, transcription-associated amplification uses two-types of primers (one referred to as a promoter-primer because it contains a promoter sequence for an RNA polymerase), two enzymes (a reverse transcriptase and an RNA polymerase), substrates (deoxyribonucleoside triphosphates, ribonucleoside triphosphates) and appropriate salts and buffers in solution to produce multiple RNA transcripts from a nucleic acid template. Briefly, in the first step, a promoter-primer hybridizes specifically to a target RNA sequence and reverse transcriptase creates a first strand cDNA by extension from the 3' end of the promoter-primer. Making the cDNA available for hybridization with the second primer may be achieved by using techniques well known in the art, such as, by denaturing the duplex or using RNase H activity. Preferably, RNase H activity supplied by the reverse transcriptase degrades the RNA in the resulting DNA:RNA duplex. A second primer then binds to the cDNA and a new strand of DNA is synthesized from the end of the second primer using the reverse transcriptase, to create a double-stranded DNA having a functional promoter sequence at one end. The RNA polymerase binds to the double-stranded promoter sequence and transcription produces multiple transcripts or "amplicons." These amplicons then are used in the transcription-associated amplification process, each serving as a template for a new round of replication, thus generating large amounts of single-stranded amplified nucleic acid (about 100 to about 3,000 copies of RNA transcripts synthesized from a single template). Preferably, amplification uses substantially constant reaction conditions (i.e., is substantially isothermal).

Primer sequences (SEQ ID NO:1 to SEQ ID NO:34, SEQ ID NO:37) bind specifically to a target sequence or a complement of a target sequence, although primer sequences may contain sequences that do not bind to the target sequence or its complement. In particular, T7 promoter primers (SEQ ID NO:7 to SEQ ID NO:12) include a T7 promoter sequence (shown separately in SEQ ID NO:36) attached to the portion of the primer sequence that binds to the target or its complement. Those skilled in the art will appreciate that a target-specific primer sequence, with or without an attached promoter sequence (SEQ ID NO:1 to SEQ ID NO:6), may be useful as a primer in a variety of in vitro amplification conditions.

Preferred methods of the present invention are described in the examples that follow. Briefly, the assays include the steps of providing a biological sample containing the target *Mycobacterium* rRNA, target capture of the rRNA, in vitro nucleic acid amplification and detection of the amplified nucleic acid products. In preferred embodiments that use transcription-mediated amplification (TMA), the final amplification mixture includes the captured target rRNA, at least one T7 promoter primer that includes a target-specific sequence and a T7 promoter sequence, at least one second (non-T7) primer that hybridizes specifically to a first strand cDNA made from the target using the T7 promoter primer, and substrates and cofactors for enzymatic polymerization by reverse transcriptase and T7 RNA polymerase in the mixture. The captured target rRNA does not have to be separated from the solid support for use in the TMA reaction. The T7 promoter sequence, when double-stranded, serves as a functional promoter for T7 RNA polymerase to produce multiple transcripts. The amplified products may be detected using any of a variety of known methods, including hybridizing the amplified products, or portions thereof, to a complementary probe sequence. The probe which includes a sequence that hybridizes specifically to a portion of the target region that is amplified using the two amplification oligonucleotides. In some embodiments, a labeled probe is used to detect the amplified products, whereas in other embodiments, the amplified products are labeled and hybridized to immobilized probes, preferably many probes present in an array. The complex of the probe and the hybridized amplified product is then detected.

More specifically, a typical assay used the following steps and conditions.

A sample (e.g., 0.5 ml of sputum sediment or bacterial culture, for positive control reactions, an equal volume of water or buffer containing a known amount of rRNA) was mixed with an equal volume of a 2× lysis buffer (e.g., 20 mM HEPES, 0.5% (w/v) lithium lauryl sulfate, pH 8) in a tube. To release nucleic acids from the bacteria, the mixture was vortexed in the presence of glass beads, or sonicated for 15 min, and then organisms remaining unlysed were heat killed by incubating at 95° C. for 15 min.

Generally 250 µl of the lysate was used in the target capture step in a new tube. To capture the target rRNA, the mixture included 250 µl of prepared sample, 250 µl of a target capture solution containing 5 pmols of SEQ ID NO:35, and 50 µg of paramagnetic particles (0.7-1.05µ particles, Seradyn, Indianapolis, Ind.) with attached immobilized poly-dT$_{14}$ probe. Immobilized probes were attached using standard carbodiimide chemistry methods (Lund, et al., 1988, *Nuc. Acids Res.* 16:10861-10880). The target capture mixture was heated at 60° C. for about 20 min and then cooled to room temperature to allow hybridization. A magnetic field was applied for 5 min to attract the magnetic particles with the attached complex containing the target RNA to a location on the reaction container (substantially as described in U.S. Pat. No. 4,895,650). The particles were then washed twice with 1 ml of a washing buffer (10 mM HEPES, 6.5 mM NaOH, 1 mM EDTA, 150 mM NaCl, 0.1% (w/v) sodium lauryl sulfate) by resuspending the particles in the buffer and then repeating the magnetic separation step.

For transcription mediated amplification, performed substantially as described previously (Kacian et al., U.S. Pat. Nos. 5,399,491 and 5,554,516), washed particles were suspended in 75 µl of amplification reagent solution (1.1 mM rUTP, 4 mM rATP, 2.7 mM rCTP, 6.7 mM rGTP, 0.67 mM each dNTP, 13.3 mM KCl, 47 mM Tris, 17.1 mM MgCl) and at least two primer oligomers (at least one promoter primer and a second primer, usually at 0.08 µM final concentration), and covered with a layer (200 µl) of inert oil to prevent evaporation. The mixture was incubated at 42° C. for 5 min, and then 25 µl of enzyme reagent was added (containing 2800 U of MMLV reverse transcriptase and 2000 U of T7 RNA polymerase per reaction, in a buffer containing 50 mM HEPES, 1 mM EDTA, 10% (v/v) Triton™ X-100, 120 mM KCl, 20% (v/v) glycerol). The mixture was shaken gently and further incubated at 42° C. for 1 hr. Negative controls consisted of all of the same reagents but substituting an equal volume of water or buffer that contained no target nucleic acid.

Amplified *Mycobacterium* sequences were detected, in some cases, using an acridinium ester (AE)-labeled probe which was detected by chemiluminescence in a suitable luminometer (e.g., LEADER™ luminometer, Gen-Probe Incorporated, San Diego, Calif.) and expressed in relative light units (RLU) substantially as described previously (U.S. Pat. No. 5,658,737 at column 25, lines 27-46; Nelson et al., 1996, *Biochem.* 35:8429-8438 at 8432). Generally, the average (mean) of detected RLU for replicate assays are reported. The probes were: for *M. tuberculosis* detection, SEQ ID NO:39 (GTCTTGTGGTGGAAAGCGCTTTAG), for *M. avium* detection, SEQ ID NO:40 (GGACCTCAAGACGCATGTC), for *M. xenopi* detection, SEQ ID NO:41 (TAGGACCATTCTGCGCATGTG), and for *M. gastri* and *M. kansasii*, SEQ ID NO:42 (TAGGACCACTTGGCGCATGCC).

In other cases, the amplified sequences were detected on an immobilized array of DNA probes specific for detection of *Mycobacterium* sequences, as described in detail previously (A. Troesch et al, 1999, *J. Clin. Microbiol.* 37(1): 49-55). The analysis was perfomed on the GeneChip™ instrumentation system (Affymetrix, Santa Clara, Calif.) to detect the intensity and pattern of fluorescent signals (expressed as relative fluorescence units or RFU) on the hybridized array. This system comprises a GeneChip™ fluidics station and the GeneArray™ scanner (Hewlett-Packard, Palo Alto, Calif.) and GeneChip™ analysis software, an algorithm to determine nucleotide base calling and determine the nucleic acid sequence present in the amplified nucleic acid. The system generates a report of the most likely *Mycobacterium* species present.

The following non-limiting examples demonstrate aspects of preferred embodiments of the present invention.

EXAMPLE 1

In Vitro Amplification of *M. tuberculosis* rRNA Using Different Primer Combinations Using the amplification and labeled probe detection methods described above, the efficiencies of transcription-mediated amplification using different combinations of T7 promoter primers and second primers were tested. The target sequences for these assays were synthetic transcripts of *M. tuberculosis* rRNA sequences, provided at $10^2$, $10^3$ or $10^6$ copies per in vitro amplification reaction. Amplification was assessed based on the detected RLU. Table 1 presents the results obtained with these combinations of amplification oligonucleotides for the amount of target copies provided, shown in parentheses for each RLU result presented. Each result represents a single assay.

TABLE 1

Detected RLU following amplification of *M. tuberculosis* rRNA ($10^2$, $10^3$ or $10^6$ copies/reaction)

| Promoter Primer | Second Primer | | | |
| --- | --- | --- | --- | --- |
| | SEQ ID NO: 15 | SEQ ID NO: 13 | SEQ ID NO: 14 | SEQ ID NO: 16 |
| SEQ ID NO: 8 | $2.5 \times 10^6$ ($10^6$) | $0.7 \times 10^6$ ($10^3$) | $0.8 \times 10^5$ ($10^3$) | Not Tested |
| | $2.2 \times 10^5$ ($10^3$) | $4.5 \times 10^5$ ($10^3$) | | |
| SEQ ID NO: 7 | $3.2 \times 10^6$ ($10^6$) | $2.4 \times 10^6$ ($10^3$) | $2.0 \times 10^6$ ($10^3$) | $3.2 \times 10^6$ ($10^3$) |
| | $3.0 \times 10^6$ ($10^3$) | $1.0 \times 10^6$ ($10^3$) | | $1.2 \times 10^6$ ($10^2$) |
| SEQ ID NO: 9 | $1.5 \times 10^6$ ($10^6$) | $0.4 \times 10^6$ ($10^3$) | $0.7 \times 10^6$ ($10^3$) | Not Tested |
| | $1.3 \times 10^6$ ($10^3$) | $0.8 \times 10^6$ ($10^3$) | | |
| SEQ ID NO: 12 | $1.4 \times 10^6$ ($10^6$) | Not Tested | Not Tested | Not Tested |
| SEQ ID NO: 10 | Not Tested | Not Tested | Not Tested | $0.8 \times 10^6$ ($10^2$) |
| SEQ ID NO: 11 | Not Tested | Not Tested | Not Tested | $0.8 \times 10^6$ ($10^2$) |

Signals of 5×10$^4$ or greater RLU are considered positive. Thus, these results show that all of the tested combinations of promoter primers and primers amplified the target *Mycobacterium* sequence, with as few as 102 copies of target present in the reaction.

EXAMPLE 2

In Vitro Amplification of *Mycobacterium* Species Using Combinations of Primers Using similar amplification and detection methods as described above and in Example 1, various combinations of T7 promoter primers and non-T7 second primers were tested using target 16S rRNA isolated from a variety of *Mycobacterium* species (*M. tuberculosis, M. bovis, M. avium, M. gastri, M. intracellulare, M. scrofulaceum, M. xenopi* and *M. kansasii*). The bacteria were obtained from the American Type Culture Collection (ATCC, Manassas, Va.) or the "DSM" culture collection (see Table 2 for accession numbers) and grown in vitro using standard microbiology methods.

In one set of experiments, the target capture and amplification reactions were performed using about 10$^4$ lysed bacteria per reaction (equivalent to about 10$^7$ copies of rRNA per reaction). The amplification reactions used a T7 promoter primer of SEQ ID NO:11) and a non-T7 second primer of SEQ ID NO:16. The RLU results obtained for the amplification products for each species of target are shown in Table 2. These results show that a single combination of two primer sequences can amplify 16S rRNA target sequences from many species of *Mycobacterium* (the source reference number for each species tested is shown in parentheses). Results of 5×10$^4$ or greater RLU are considered positive.

TABLE 2

RLU Detected for *Mycobacterium* species Target Sequences Amplified Using SEQ ID NO: 11 and SEQ ID NO: 16

| Target 16S rRNA Source | Detected RLU |
|---|---|
| *M. tuberculosis* (ATCC 27294) | 4.0 × 10$^6$ |
| *M. bovis* (ATCC 19274) | 4.2 × 10$^6$ |
| *M. avium* (DSM 43216) | 1.8 × 10$^6$ |
| *M. intracellulare* (ATCC 15985) | 7.5 × 10$^6$ |
| *M. kansasii* (DSM 43224) | 2.5 × 10$^6$ |
| *M. gastri* (ATCC 15754) | 2.7 × 10$^6$ |
| *M. xenopi* (ATCC 19250) | 1.0 × 10$^6$ |
| *M. scrofulaceum* (ATCC 19981) | 2.8 × 10$^6$ |

To further demonstrate that primers of the present invention are not species-limited for amplification in vitro, additional combinations of T7 promoter primers and non-T7 second primers were similarly tested but using different amounts of target per reaction. In these assays, the T7 promoter primer had the sequence of SEQ ID NO:11, and was combined with second primers having the sequences of SEQ ID NO:13, SEQ ID NO:17, SEQ ID NO:18, SEQ ID NO:19 or SEQ ID NO:20. The results are shown in Table 3. These results show that different combinations of promoter primer and second primers can also amplify 16S rRNA sequences from a variety of *Mycobacterium* species.

TABLE 3

RLU Detected for *Mycobacterium* species Target Sequences Amplified Using SEQ ID NO: 11 and Different Second Primers

| Target Source | Second Primers (SEQ ID NO) | | | | |
|---|---|---|---|---|---|
| Copies/reaction | NO: 13 | NO: 17 | NO: 18 | NO: 19 | NO: 20 |
| *M. tuberculosis* | | | | | |
| 10$^5$ | <10$^6$ | 2.7 × 10$^6$ | 2.1 × 10$^6$ | 2.7 × 10$^6$ | Not tested |
| 10$^2$ | Not tested | 1.2 × 10$^6$ | 4.0 × 10$^5$ | 2.5 × 10$^5$ | Not tested |
| *M. intracellulare* | | | | | |
| 10$^5$ | 4.0 × 10$^5$ | 2.3 × 10$^6$ | Not tested | 5.0 × 10$^5$ | Not tested |
| *M. xenopi* | | | | | |
| 10$^5$ | Not tested | 3.0 × 10$^4$ | Not tested | Not tested | 3.0 × 10$^6$ |
| *M. kansasii* | | | | | |
| 10$^5$ | Not tested | Not tested | <10$^4$ | Not tested | Not tested |

EXAMPLE 3

In Vitro Amplification of *Mycobacterium* Species Using Different Non-T7 Second Primers and Detection of Species Using Probe Arrays This example shows that other non-T7 second primers, used in combination with a T7 promoter primer having a sequence of SEQ ID NO:11, can also amplify 16S rRNA sequences from a variety of *Mycobacterium* species. In these experiments, the efficiency of amplification was measured by using an AE-labeled probe, as in Examples 1 and 2. In addition, amplified nucleic acids from these amplification reactions were cleaved and fluorescently labeled in vitro using methods substantially as described in PCT International Pat. App. No. PCT/FR99/01469. Then the labeled amplified nucleic acid was contacted to a GeneChip™ (Affymetrix) containing an array of sequence-specific probes that bind to sequences present in *Mycobacterium* 16S rRNA, substantially as described above (Troesch et al., 1999, J. Clin. Microbiol. 3791): 49-55). The hybridized labeled fragments on the probe array were washed to remove unhybridized nucleic acids and contaminants and the hybridized nucleic acids were detected as fluorescent signal in a pattern that corresponds to the sequences of the probes on the array, referred to as "base calling." This method was used to identify the species of *Mycobacterium* represented by the amplified nucleic acid. Because, in these assays, the source of the target rRNA provided was known, the percentage of correct base calling for that target species was reported as a measure of the accuracy of amplification and detection of the amplified nucleic acid.

The cumulative results of these tests are shown in Table 4. These results show that additional combinations of primers can amplify 16S rRNA target obtained from different *Mycobacterium* species and the *Mycobacterium* species can then be identified by detecting the amplified nucleic acid on an array of probes, such that the cumulative pattern of hybridization complexes determines the source of the target sequence.

TABLE 4

| Non-T7 Primer | Target Source | RLU/copies of rRNA | % Base Calling |
|---|---|---|---|
| SEQ ID NO: 16 | M. tuberculosis | $4 \times 10^6/500$ | Not tested |
| | M. tuberculosis | $5.7 \times 10^6/10^4$ | Not tested |
| | M. intracellulare | $3 \times 10^6/10^4$ | Not tested |
| | M. scrofulaceum | $5 \times 10^5/10^5$ | Not tested |
| | M. terrae | $1 \times 10^4/10^5$ | Not tested |
| SEQ ID NO: 37 | M. xenopi | $4 \times 10^6/10^5$ | 95 |
| | M. tuberculosis | $5 \times 10^6/10^5$ | 98 |
| SEQ ID NO: 30 | M. xenopi | $3.7 \times 10^6/10^5$ | 97 |
| | M. tuberculosis | $5.2 \times 10^6/10^5$ | 99 |
| SEQ ID NO: 29 | M. xenopi | $4 \times 10^6/10^5$ | 88 |
| SEQ ID NO: 28 | M. xenopi | $3.7 \times 10^6/10^5$ | 97 |
| SEQ ID NO: 27 | M. xenopi | $3.7 \times 10^6/10^5$ | 97 |
| SEQ ID NO: 31 | M. xenopi | $4 \times 10^6/10^5$ | 94 |
| SEQ ID NO: 32 | M. xenopi | $3.1 \times 10^6/10^5$ | 90 |
| SEQ ID NO: 33 | M. xenopi | $3.3 \times 10^6/10^5$ | 91 |
| SEQ ID NO: 34 | M. xenopi | $1.2 \times 10^6/10^5$ | Not tested |
| SEQ ID NO: 24 | M. xenopi | $3.1 \times 10^6/10^5$ | 90 |
| SEQ ID NO: 29 | M. xenopi | $1.1 \times 10^6/10^5$ | Not tested |
| SEQ ID NO: 21 | M. celatum | $2.3 \times 10^5/10^5$ | 94 |
| SEQ ID NO: 22 | M. celatum | $1.2 \times 10^5/10^5$ | 73 |
| SEQ ID NO: 23 | M. celatum | $4.4 \times 10^5/10^5$ | 97 |
| SEQ ID NO: 25 | M. celatum | $1.1 \times 10^6/10^5$ | 78 |
| SEQ ID NO: 26 | M. celatum | $1.3 \times 10^5/10^5$ | Not tested |

In separate experiments, amplification by TMA was tested by varying amounts of target (0, 10, 100 and 1000 copies of *M. tuberculosis* 16S rRNA target sequence) and of enzymes used in the amplification mixture (1500 U of RT plus 2000 U T7 RNA polymerase or 2000 U each of RT and T7 RNA polymerase). Amplification efficiency was monitored by detecting binding of an AE-labeled probe as described above. Under these conditions, the negative control (0 copies of amplicon) provided a background level of signal (about 2000-3000 RLU), while all of the target-containing amplification mixtures provided significantly higher signal ($4 \times 10^5$ to $5 \times 10^6$ RLU). For samples containing only 10 copies of target sequence, reaction mixtures containing 2000 U each of RT and T7 RNA polymerase, provided somewhat higher detectable levels of amplified product ($1.3 \times 10^6$ RLU, mean of five reactions) than seen with the reaction mixtures containing 1500 U of RT plus 2000 U T7 RNA polymerase ($4 \times 10^5$ RLU). For samples containing 100 or 1000 copies of the target sequence, the detectable levels of amplified products were substantially equivalent for both concentrations of enzyme concentrations tested ($4-5 \times 10^6$ RLU).

EXAMPLE 4

Amplification of *Mycobacterium* 16S rRNA Using a Modified Primer

To improve the efficien of in vitro nucleic acid amplification of 16S rRNA target sequences derived from *M. xenopi*, a non-T7 second amplification primer was modified to include a modified "K-base" (Lin & Brown, 1992, Nucleic Acids Res. 20: 5149-5152). Initially, the modified primer was used was that of SEQ ID NO:16 in which the $25^{th}$ residue was modified to be the K-base (SEQ ID NO:38) and the target was *M. tuberculosis* 16S rRNA. Use of this modified non-T7 primer oligonucleotide resulted in significant improvement in amplification of *M. xenopi* target when $10^6$ copies of the 16S rRNA target sequence were present in the reaction, as shown by the results in Table 5, which present the average (mean) RLU detected for amplification products detected as described above using an AE-labeled probe. The amplification reactions were performed substantially as described above for each of the different target sequences using a combination of primers of SEQ ID NO:8 and SEQ ID NO:16 or SEQ ID NO:8 and SEQ ID NO:38, the latter being the primer containing the K-base modification described above. The results are the average of four amplification reactions for *M. tuberculosis* target sequences ($10^3$ copies per reaction) and six amplification reactions for *M. xenopi* target sequences ($10^6$ copies per reaction). Negative controls contained water in place of target nucleic acid.

The results in Table 5 show that primers that contain modified K-base residues may increase in vitro amplification efficiency of a target sequence when compared to a similar primer sequence that does not contain a modified base.

TABLE 5

Amplicons Detected (mean RLU) for Different Targets Using Modified or Unmodified Primers

| Target Species | Primers: SEQ ID NO: 8 + SEQ ID NO: 16 | Primers: SEQ ID NO: 8 + SEQ ID NO: 38 |
|---|---|---|
| M. tuberculosis | $5.00 \times 10^6$ | Not Done |
| M. xenopi | $1.56 \times 10^4$ | $9.45 \times 10^5$ |
| Negative Control | $5.6 \times 10^3$ | $6.0 \times 10^3$ |

EXAMPLE 5

PCR Amplification Using *Mycobacterium* Specific Primers

This example shows the specificity of primers of the present invention when used in PCR amplification and detection of the amplified DNA on a solid support having an array of immobilized probes (GeneChip™). For target preparation, M. tuberculosis (ATCC 27294) and M. xenopi (ATCC 19250) strains were grown in vitro using standard microbiology methods. Bacterial stock suspensions were made in water and adjusted to a concentration of about $6 \times 10^8$ bacteria per ml and successive dilutions in water were made to produce a solution of $10^4$ bacteria per µl (equivalent to 104 copies of bacterial DNA per µl) which then inactivated by heating for 15 min at 95° C. For amplification, sterile water was used as a negative control.

PCR amplification was carried out in a microtitre 96-well plate using a individual 45 µl reactions containing 50 mM KCl, 10 mM Tris (pH 8.3), 1.5 mM MgCl2, 0.001% (wt/vol) gelatin, 5% (vol/vol) dimethylsulfoxide, 0.33 µM of each primer in a pair of primers per reaction, 200 µM of each dNTP, and 0.75 U of Taq polymerase (AmpliTaq™; Perkin-Elmer, Norwalk, Conn.) Thermal cylcing was performed in a Perkin-Elmer 9600™ thermal cycler with an initial denaturation step at 94° C. for 5 min, followed by 30 cycles of 94° C. for 1 min, 55° C. for 1 min and 72° C. for 1 min, and a final cycle of 72° C. for 10 min.

Following PCR amplification, the amplification products were analyzed by agarose gel electrophoresis, to detect the presence or absence of a band of DNA of about 300 nt in size. No band was visible on the gel for the negative control (water in place of target DNA) for any combination of primers. For the combination of primers having SEQ ID NO:11 and SEQ ID NO:16, a band of amplified DNA was seen when M. tuberculosis was the target but no bands was seen when M. xenopi was the target DNA provided. In contrast, when primers having SEQ ID NO:11 and SEQ ID NO:37, or SEQ ID NO:11 and SEQ ID NO:30 were used, no band of amplified DNA was seen when M. tuberculosis was the target but the expected band was seen when M. xenopi was the target DNA provided.

Next, the amplification products of the PCR reactions were detected on a solid support having attached sequence-specific probes in a two-dimensional array (GeneChip™), substantially as described previously (Troesch et al., 1999, J. Clin. Microbiol., 37(1):49-55, 1999). For detection, promoter-tagged PCR amplicons were used for generating labeled single-stranded RNA targets by in vitro transcription reactions (20 µl) that each contained approximately 50 ng of PCR product; 20 U of T7 RNA polymerase (Promega); 40 mM Tris acetate (pH 8.1); 100 mM Mg(acetate)$_2$; 10 mM dithiothreitol; 1.25 mM each of ATP, CTP, and GTP; 0.5 mM UTP; and 0.25 mM fluorescein-UTP. Transcription reactions were incubated at 37° C. for 1 hr and then the labeled RNA was hybridized to the probe array and analyzed as described (Troesch et al., supra).

For hybridization, 5 µl the labeled RNA target was diluted in 700 µl of hybridization buffer (0.90 M NaCl, 60 mM NaH$_2$ PO$_4$, 6 mM EDTA, pH 7.4, and 0.05% (vol/vol) Triton X-100), applied to the probe array and incubated for 30 min at 45° C. Then the probe array was washed twice in 3×SSPE (0.45 M NaCl, 30 mM NaH$_2$ PO$_4$, 3 mM EDTA, pH 7.4) and 0.005% (vol/vol) Triton™ X-100 at 30° C. and the fluorescent signal emitted by labeled RNA bound to the array was detected. The detected signal intensities (mean, median and maximum RFU), nucleotide base call (% base call) and sequence determinations were generated by using an algorithm (GeneChip™ software, Affymetrix). A candidate selection index was determined by the percentage of homology between the experimentally derived sequence and reference sequences present on the array. The results are shown in Table 6.

TABLE 6

| Amplification Primers | Target DNA | Identified Species | % Base calling | Mean RFU | Median RFU | Maximum RFU |
|---|---|---|---|---|---|---|
| SEQ ID NO: 11 SEQ ID NO: 16 | Water (negative control) | None | 13.5 | 79 | 71 | 224 |
| SEQ ID NO: 11 SEQ ID NO: 16 | M. Tuberculosis | M. Tuberculosis | 98.4 | 9838 | 8864 | 26192 |
| SEQ ID NO: 11 SEQ ID NO: 37 | Water (negative control) | None | 10.3 | 32 | 37 | 59 |
| SEQ ID NO: 11 SEQ ID NO: 37 | M. Xenopi | M. Xenopi | 94.6 | 13482 | 12055 | 32759 |
| SEQ ID NO: 11 SEQ ID NO: 30 | Water (negative control) | None | 9.7 | 47 | 46 | 88 |
| SEQ ID NO: 11 SEQ ID NO: 30 | M. Xenopi | M. Xenopi | 91.9 | 21455 | 19892 | 45531 |

These results show that the amplification primers efficiently and specifically amplified the intended target DNA. Moreover, the amplified sequences could be used in a probe hybridization assay to detect and identify the source of the nucleic acid from which the amplicons were produced.

EXAMPLE 6

Amplification of Many *Mycobacterium* Species 16S rRNA Sequences Using a Combination of Primers This example shows the specificity of primers of the present invention when used in TMA amplification and detection on a solid support having an array of a large number of immobilized sequence-specific probes (GeneChip™). The conditions for sample preparation were substantially the same as described above for a typical assay except that the target capture solution contained 5 pmoles of SEQ ID NO:35, the washing buffer for the particles was 10 mM HEPES, 1 mM EDTA, 150 mM NaCl and 0.1% (w/v) sodium lauryl sulfate, pH 7.5. The washed particles were resuspended in 25 µl of sterile water.

The amplification conditions were as follows. To the particles in water were added 50 µl of amplification reagent solution (1.6 mM rUTP, 4 mM rCTP, 6 mM rATP, 10 mM rGTP, 1 mM each dNTP, 80 mM Tris, 35 mM KCl and 25.6 mM MgCl2) and three primers (SEQ ID NO:11, SEQ ID NO:16, SEQ ID NO:37), each at a concentration of 0.08 µM per reaction. The solution was mixed and covered with 200 µl of inert oil to prevent evaporation. The amplification mixture was incubated for 10 min at 60° C., then for 5 min at 42° C., and 25 µl of enzyme reagent was added (2000 U of reverse transcriptase and 2000 U of T7 polymerase). The mixture was shaken gently and further incubated for 1 h at 42° C.

The amplified *Mycobacterium* sequences were cleaved and fluorescently labeled as described in Example 3 and detected on a DNA probe array as described in Example 6. The results are summarized in Table 7 for many *Mycobacterium* species (the American Type Culture Collection (ATCC, Manassas, Va., USA) source numbers are shown in parentheses following the species name). For each species tested, the results are show as the indentified species based on the base calling on the DNA probe chip (i.e., % correct base calling for a particular species) and the average signal intensity for the detected signal (mean relative fluorescence units or RFU) is shown.

TABLE 7

Amplification and Detection of Many *Mycobacterium* Species Using a Single Combination of Primers

| *Mycobacterium* species | Identified Species | Base calling | Mean RFU |
| --- | --- | --- | --- |
| Abscessus (ATCC 19977) | abscessus | 97.8% | 1702 |
| Africanum (ATCC 25420) | tuberculosis | 98.4% | 6 519 |
| Asiaticum (ATCC 25276) | asiaticum | 97.8% | 4 530 |
| avium (ATCC 25291) | avium | 99.5% | 752 |
| bovis (ATCC 19274) | tuberculosis | 100.0% | 4 390 |
| Celatum (ATCC 51130) | celatum | 96.2% | 657 |
| Celatum (ATCC 51131) | celatum | 97.8% | 4 751 |
| Chelonae (ATCC 14472) | chelonae | 98.4% | 2 845 |
| Chelonae mucogenicum (ATCC 49649) | chelonae | 98.4% | 990 |
| Chelonae (ATCC 35752) | chelonae | 97.8% | 2 440 |
| Flavescens (ATCC 14474) | flavescens | 93.5% | 2 123 |
| Fortuitum (ATCC 49403) | fortuitum | 97.3% | 3 841 |
| Fortuitum (ATCC 49404) | fortuitum | 96.2% | 2 390 |
| Fortuitum/chelonae (ATCC 6841) | Fortuitum/chelonae | 96.2% | 1 936 |
| gastri (ATCC 15754) | gastri | 98.9% | 3 075 |
| Gordonae (ATCC14470) | gordonae | 94.1% | 1 329 |
| Haemophilum (ATCC33207) | haemophilum | 98.4% | 874 |
| Interjectum (ATCC 51457) | interjectum | 98.9% | 791 |
| Intermedium (DSM 44049) | intermedium | 98.9% | 1 022 |
| Intracellulare (ATCC 13950) | intracellulare | 98.4% | 741 |
| Intracellulare (ATCC 35764) | intracellulare | 98.9% | 2 387 |
| Intracellulare (ATCC 35770) | intracellulare | 95.1% | 516 |
| Kansasii (ATCC 12478) | kansasii | 98.4% | 3 170 |
| Malmoense (ATCC 29571) | malmoense | 96.8% | 1 076 |
| Marinum (ATCC 25039) | marinum | 98.9% | 8 020 |
| non-chromogenicum (ATCC 19530) | Non-chromogenicum | 98.4% | 1 230 |
| Paratuberculosis (ATCC 35767) | Paratuberculosis | 98.9% | 2 716 |
| phlei (ATCC 11758) | phlei | 98.9% | 2 532 |
| Scrofulaceum (ATCC 19981) | Scrofulaceum | 99.5% | 5 119 |
| Shimoidei (ATCC 27962) | shimodei | 94.1% | 1 459 |
| simiae (ATCC 25275) | simiae | 98.9% | 5 392 |
| Smegmatis (ATCC 14468) | smegmatis | 97.3% | 1 894 |
| szulgai (ATCC 35799) | szulgai | 98.9% | 822 |
| terrae (ATCC 15755) | terrae | 98.4% | 1 224 |
| triviale (ATCC 23292) | triviale | 98.9% | 5 975 |
| Tuberculosis (ATCC 27294) | tuberculosis | 100.0% | 3 159 |
| Ulcerans (ATCC 19423) | ulcerans | 98.9% | 3 177 |
| xenopi (ATCC 19250) | xenopi | 99.5% | 2 258 |

These results show that a single combination of primers effectively amplifies 16S rRNA sequences from many *Mycobacterium* species, allowing a relatively simple procedure to be used to detect the presence of many different species using a single assay. When combined with a detection procedure that uses probes specific for many species, such as a DNA probe array present on a GeneChip™, the assay can be used to identify many different species present in a biological sample.

The scope of the invention is defined by the claims that follow and all equivalents thereof.

The invention claimed is:

1. A method of detecting *Mycobacterium* species present in a biological sample, comprising the steps of:
   providing a biological sample containing nucleic acid from at least one *Mycobacterium* species comprising a *Mycobacterium* 16S ribosomal RNA (rRNA) or DNA encoding a *Mycobacterium* 16S rRNA;
   amplifying the *Mycobacterium* 16S rRNA or *Mycobacterium* DNA encoding the *Mycobacterium* 16S rRNA in an in vitro nucleic acid amplification mixture comprising at least one polymerase activity, and a combination of at least one first oligonucleotide and at least one second oligonucleotide, wherein the first oligonucleotide consists of a target-specific sequence that consists of SEQ ID NO:5 that is joined to a 5' promoter sequence, and the second oligonucleotide is an oligonucleotide consisting of 19 to 25 bases made up of contiguous bases 1 to 18 of SEQ ID NO:24 and optionally three to seven bases 5' to the contiguous bases 1 to 18 of SEQ ID NO:24 and/or optionally one base 3' to the contiguous bases 1 to 18 of SEQ ID NO:24 to produce amplified *Mycobacterium* nucleic acid; and
   detecting the amplified *Mycobacterium* nucleic acid by detecting a label associated with the amplified *Mycobacterium* nucleic acid.

2. The method of claim 1, further comprising In the steps of:
   adding to the biological sample at least one capture oligonucleotide that specifically hybridizes to the *Mycobacterium* 16S rRNA and an immobilized nucleic acid that hybridizes to the capture oligonucleotide under hybridizing conditions to produce a hybridization complex; and
   separating the hybridization complex from other components of the biological sample before the amplifying step.

3. The method of claim 1, wherein the amplifying step amplifies 16S rRNA or DNA encoding 16S rRNA from a *Mycobacterium* other than tuberculosis (MOTT) species.

4. The method of claim 1, wherein the amplifying step amplifies 16S rRNA or DNA encoding 16S rRNA from *M. celatum* or *M. xenopi*.

5. The method of claim 1, wherein the detecting step uses at least one probe that hybridizes specifically to the amplified *Mycobacterlum* nucleic acid.

6. The method of claim 5, wherein the detecting step uses at least one labeled probe that hybridizes specifically to the amplified *Mycobacterium* nucleic acid.

7. The method of claim 5, wherein the detecting step uses a plurality of probes that hybridize specifically to the amplified *Mycobacterium* nucleic acid.

8. The method of claim 1, wherein the amplifying step uses a combination of at least a first primer and a second primer, wherein the first primer consists of SEQ ID NO:11, and the second primer is selected from the group consisting of SEQ ID NO:21, SEQ NO:22, SEQ ID NO:23 and SEQ ID NO:24.

9. The method of claim 8, wherein the second primer consists of SEQ ID NO:21.

10. The method of claim 8, wherein the second primer consists of SEQ ID NO:22.

11. The method of claim 8, wherein the second primer consists of SEQ ID NO:23.

12. The method of claim 8, wherein the second primer consists of SEQ ID NO:24.

13. A composition for amplifying in an in vitro amplification reaction a *Mycobacterium* 16S rRNA sequence or a DNA encoding 16S rRNA, comprising a combination of at least one first oligonucleotide and at least one second oligonucleotide, wherein the first oligonucleotide consists of target-specific sequence that consists of SEQ ID NO:5 that is joined to a 5' promoter sequence, and wherein the second oligonucleotide is an oligonucleotide consisting of 19 to 26 bases made up of contiguous bases 1 to 18 of SEQ ID NO:24 and optionally three to seven bases 5' to the contiguous bases 1 to 18 of SEQ ID NO:24 and/or optionally one base 3' to the contiguous bases 1 to 18 of SEQ ID NO:24.

14. The composition of claim 13, wherein the composition comprises:
    at least one first oligonucleotide consisting of SEQ ID NO:11, and
    at least one second oligonucleotide consisting of SEQ ID NO:21, SEQ ID NO:22, SEQ ID NO:23 or SEQ ID NO:24.

15. The composition of claim 14, wherein the composition comprises:
    the at least one first oligonucleotide consisting of SEQ ID NO:11, and
    the at least one second oligonucleotide consisting of SEQ ID NO:21.

16. A kit containing at least a pair of oligonucleotides, wherein at least one first oligonucleotide consists of a target-specific sequence that consists of SEQ ID NO:5 that is mined to a 5' promoter sequence, and wherein at least one second oligonucleotide consists of a sequence selected from the group consisting of SEQ ID NO:21, SEQ ID NO:22, SEQ ID NO:23, and SEQ ID NO:24.

17. The kit of claim 16, wherein the first oligonucleotide consists of SEQ ID NO:11.

18. The kit of claim 17, wherein:
    the first oligonucleotide consists of SEQ ID NO:11, and
    the at least one second oligonucleotide consists of SEQ ID NO:21, SEQ ID NO:22, or SEQ ID NO:23.

19. The composition of claim 14, wherein the composition comprises:
    the at least one first oligonucleotide consisting of SEQ ID NO:11, and
    the at least one second oligonucleotide consisting of SEQ ID NO:23.

20. The composition of claim 14, wherein the composition comprises:
    the at least one first oligonucleotide consisting of SEQ ID NO:11, and
    the at least one second oligonucleotide consisting of SEQ ID NO:24.

* * * * *

UNITED STATES PATENT AND TRADEMARK OFFICE
CERTIFICATE OF CORRECTION

PATENT NO. : 7,294,489 B2
APPLICATION NO. : 10/665708
DATED : November 13, 2007
INVENTOR(S) : Steven T. Brentano et al.

It is certified that error appears in the above-identified patent and that said Letters Patent is hereby corrected as shown below:

In claim 16, line 4, at column 38, line 36, delete "mined" and insert instead --joined--.

Signed and Sealed this

Twenty-ninth Day of September, 2009

David J. Kappos
*Director of the United States Patent and Trademark Office*